United States Patent
Rebinsky

(10) Patent No.: US 9,790,883 B2
(45) Date of Patent: Oct. 17, 2017

(54) SYSTEM FOR SENSING AND CONTROLLING FUEL GAS CONSTITUENT LEVELS

(71) Applicant: Caterpillar Inc., Peoria, IL (US)

(72) Inventor: Douglas Alexander Rebinsky, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 182 days.

(21) Appl. No.: 14/807,205

(22) Filed: Jul. 23, 2015

(65) Prior Publication Data
US 2017/0022919 A1    Jan. 26, 2017

(51) Int. Cl.
| | |
|---|---|
| G01N 25/36 | (2006.01) |
| G01N 27/18 | (2006.01) |
| F02D 41/14 | (2006.01) |
| F02D 41/26 | (2006.01) |
| F02M 21/02 | (2006.01) |

(Continued)

(52) U.S. Cl.
CPC ....... *F02D 41/1494* (2013.01); *F02D 19/029* (2013.01); *F02D 19/0634* (2013.01); *F02D 19/0671* (2013.01); *F02D 41/0027* (2013.01); *F02D 41/1446* (2013.01); *F02D 41/26* (2013.01); *F02M 21/0206* (2013.01); *F02M 21/0215* (2013.01); *F02M 21/0227* (2013.01); *G01N 25/36* (2013.01); *G01N 27/18* (2013.01); *G01N 33/225* (2013.01); *F02D 13/0215* (2013.01); *F02D 2200/0611* (2013.01)

(58) Field of Classification Search
CPC ...... G01N 25/20; G01N 25/36; G01N 25/488; G01N 27/18; G01N 27/185
USPC .......................................... 73/25.03; 123/527
See application file for complete search history.

(56) References Cited

U.S. PATENT DOCUMENTS

| | | |
|---|---|---|
| 5,177,696 A | 1/1993 | Bonne |
| 5,311,447 A | 5/1994 | Bonne |

(Continued)

FOREIGN PATENT DOCUMENTS

| | | |
|---|---|---|
| DE | 19908885 A1 | 9/2000 |
| EP | 2522972 A2 | 11/2012 |

(Continued)

*Primary Examiner* — Erick Solis
(74) *Attorney, Agent, or Firm* — Finnegan, Henderson, Farabow, Garrett & Dunner LLP

(57) ABSTRACT

A system for sensing and controlling a fuel gas composition may include a plurality of micro-sensors mounted in a single chamber, with each of the micro-sensors being configured to sense a characteristic of a mixture of gaseous fuel introduced into the chamber. The system may also include a plurality of heating elements, with each of the heating elements being associated with one of the plurality of micro-sensors, and the plurality of heating elements being configured to implement a different temperature level at each of the micro-sensors. The system may also include a microprocessor configured to determine a thermodynamic property of the mixture of gaseous fuel at the different temperature levels at each of the micro-sensors as a function of the characteristic sensed by each micro-sensor, correlate the thermodynamic property to a fuel gas composition of the mixture of gaseous fuel, and control an amount of at least one constituent in the mixture of gaseous fuel as a function of the fuel gas composition determined by the correlation.

20 Claims, 3 Drawing Sheets

(51) Int. Cl.
    *F02D 19/02*     (2006.01)
    *F02D 19/06*     (2006.01)
    *F02D 41/00*     (2006.01)
    *G01N 33/22*     (2006.01)
    *F02D 13/02*     (2006.01)

(56) References Cited

U.S. PATENT DOCUMENTS

| | | | | |
|---|---|---|---|---|
| 5,333,591 | A * | 8/1994 | Korsmeier | F02B 43/00 |
| | | | | 123/527 |
| 5,971,745 | A * | 10/1999 | Bassett | F23N 1/022 |
| | | | | 431/12 |
| 6,474,137 | B1 * | 11/2002 | Hammond | G01N 9/24 |
| | | | | 73/24.01 |
| 7,356,420 | B2 | 4/2008 | Vilanova et al. | |
| 8,043,566 | B2 | 10/2011 | Morris | |
| 2007/0013013 | A1 | 1/2007 | Zemskova et al. | |
| 2009/0035870 | A1 * | 2/2009 | Ruiz | G01N 25/20 |
| | | | | 436/147 |
| 2015/0090222 | A1 * | 4/2015 | Rebinsky | F02D 41/3005 |
| | | | | 123/435 |

FOREIGN PATENT DOCUMENTS

| | | |
|---|---|---|
| JP | S58113545 A | 7/1983 |
| JP | H07294467 A | 11/1995 |

\* cited by examiner

SYSTEM FOR SENSING AND CONTROLLING FUEL GAS CONSTITUENT LEVELS

TECHNICAL FIELD

The present disclosure relates generally to a system for sensing fuel gas constituent levels and, more particularly, to a system for sensing and controlling fuel gas constituent levels in a gaseous fuel mixture supplied to an engine.

BACKGROUND

Gaseous fuel powered engines can operate using a range of different fuel mixtures. Different fuel mixtures may result in different quantities of pollutants such as Nitrogen Oxide and Nitrogen Dioxide (collectively referred to as $NO_x$) being produced during combustion. Various environmental regulations have resulted in a need to significantly reduce the levels of pollutants without restricting the performance of an engine, such as measured by the maximum Brake Mean Effective Pressure (BMEP). Stoichiometric combustion can be used in some combustion engines, along with special catalysts in the exhaust aftertreatment system, to reduce levels of $NO_x$ produced during combustion. However, this may result in high combustion temperatures and increased knock propensity, which restricts the BMEP of the engine. Therefore, various alternative methods of reducing levels of pollutants such as $NO_x$ produced during combustion may include accurate control of the amounts of various constituents in the fuel, such as by controlling the amounts of $H_2$ in the fuel. Accurate sensing and control of the composition of the fuel and of operating characteristics of the engine enables improved performance and reduced production of pollutants. Catalytic partial oxidation reforming (CPOx) is one method that may be used during operation of an engine in order to change the levels of $H_2$ provided to the air-fuel mixture during combustion, thereby improving thermal efficiency and combustion stability.

Traditionally, a determination of the physical properties of gaseous fuel used to power combustion engines was achieved by temperature and/or pressure control of the gaseous fuel, or by means of compositional analysis such as performed using gas chromatography without control of the temperature or pressure. Methods for measuring the quality and composition of gaseous fuels enable a determination of the heating value available from a particular gaseous fuel mixture. An engine using the particular gaseous fuel mixture of determined quality and heating value can be operated by, for example, controlling ignition and fuel injection in order to maintain or improve power output and reduce production of pollutants. Some existing techniques for continuously analyzing a stream of gaseous fuel during operation of an engine use expensive measuring equipment that requires ongoing maintenance and lacks reliability under harsh field operating conditions.

One attempt to address the above-described problems is disclosed in U.S. Pat. No. 5,311,447 (the '447 patent) that issued to Bonne on May 10, 1994. In particular, the '447 patent discloses a non-combustion process for measuring the quality of fuel being fed to a gas consumption device. The method includes diverting a portion of the fuel through a sensor chamber, and measuring a viscosity of the fuel at a first sensor in the chamber. The method also includes measuring a thermal conductivity of the fuel with a second sensor in the chamber, at two different temperature levels. The viscosity and thermal conductivity values are then corrected based on a temperature and a pressure of the fuel, and a corresponding heating value is determined using an empirical formula determined as a function of the corrected viscosity and thermal conductivity values. The heating value is then stored, displayed, or given off as a control pulse depending on the information required for a particular application. The empirical formula used to calculate the heating value of the fuel is determined through the use of a commercially available regression analysis program.

Although the method described in the '447 patent may be adequate in some applications, it may be less than optimal. For example, the method relies on determination of at least two different fuel gas properties, such as viscosity and thermal conductivity, and then derivation of a characteristic of the fuel gas such as heat content using the two determined properties. As a result, the associated system requires at least two different types of sensors, adding to expense, and may have relatively slow response times dependent upon measurement of different fuel characteristics. The speed of the system may preclude its use in highly-transient applications (e.g., in combustion engine applications).

The disclosed system is directed to overcoming one or more of the problems set forth above and/or other problems associated with existing systems for determining gas compositions.

SUMMARY

In one aspect, the present disclosure is directed to a system for sensing and controlling a fuel gas composition. The system may include a plurality of micro-sensors mounted in a single chamber, with each of the micro-sensors being configured to sense a characteristic of a mixture of gaseous fuel introduced into the chamber. The system may also include a plurality of heating elements, with each of the heating elements being associated with one of the plurality of micro-sensors, and the plurality of heating elements being configured to implement a different temperature level at each of the micro-sensors. The system may still further include a microprocessor configured to determine a thermodynamic property of the mixture of gaseous fuel at the different temperature levels at each of the micro-sensors as a function of the characteristic sensed by each micro-sensor, correlate the thermodynamic property to a fuel gas composition of the mixture of gaseous fuel, and control an amount of at least one constituent in the mixture of gaseous fuel as a function of the fuel gas composition determined by the correlation.

In another aspect, the present disclosure is related to a control system for use with an engine. The control system may include a plurality of micro-sensors mounted in a single micro-chamber and configured to sense a characteristic of a mixture of gaseous fuel introduced into the micro-chamber, and a plurality of resistive heating elements associated with each of the plurality of micro-sensors and configured to implement a different temperature level at each of the plurality of micro-sensors. The system may also include a microprocessor configured to determine a thermodynamic property of the mixture of gaseous fuel at the different temperature levels at each of the micro-sensors as a function of the characteristic sensed by each micro-sensor, correlate the thermodynamic property to a fuel gas composition of the mixture of gaseous fuel, control an amount of at least one constituent in the mixture of gaseous fuel and an operating parameter of the engine as a function of the fuel gas composition determined by the correlation.

In another aspect, the present disclosure is directed to a method of controlling an engine. The method may include diverting successive portions of a mixture of gaseous fuel being supplied to the engine into a micro-chamber where the successive portions are each held temporarily in a substantially still condition. The method may further include heating each of a plurality of micro-sensors to a different temperature level at the same time at a plurality of different spaced locations within the micro-chamber, and determining an overall thermal conductance for each successive portion of the mixture of gaseous fuel. The method may further include selectively adjusting at least one of a level of a constituent present in the mixture of gaseous fuel and a control parameter of the engine based on the thermal conductance.

DETAILED DESCRIPTION

Figure 1:
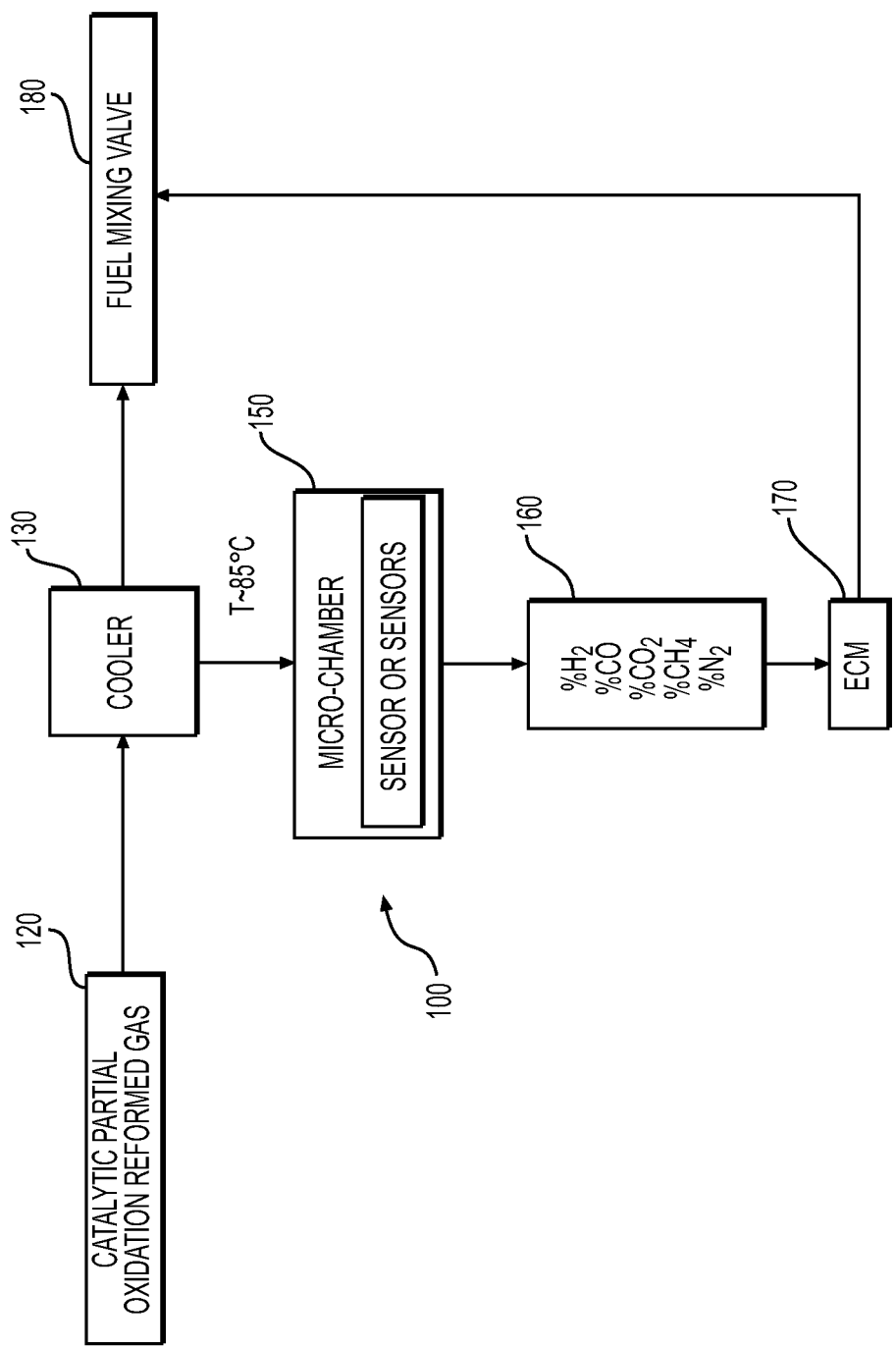
FIG. 1 is a diagrammatic illustration of an exemplary disclosed system.

FIG. 1 illustrates an exemplary system 100 for sensing and controlling the amount of one or more constituents in a gaseous fuel mixture that is supplied to an engine. By providing accurate real-time measurements of the amounts of the various constituents in the gaseous fuel mixture, the system 100 enables precise control of the combustion process to maintain or increase performance while reducing production of pollutants. A combustion engine may be, for example, a four-stroke gaseous-fueled engine that is controlled by an engine control module (ECM) 170. One skilled in the art will recognize, however, that the engine may alternatively be a two-stroke engine, if desired. The engine may include an engine block that at least partially defines one or more cylinders. A piston may be slidably disposed within each cylinder to reciprocate between a top-dead-center (TDC) position and a bottom-dead-center (BDC) position, and a cylinder head may be associated with each cylinder. The cylinder, piston, and cylinder head may together define a combustion chamber. The engine may include any number of combustion chambers disposed in an "in-line" configuration, in a "V" configuration, in an opposing-piston configuration, or in any other suitable configuration.

The gaseous fuel mixture provided to each combustion chamber in the engine may be first compressed, and then cooled, such as by a cooler 130, before being injected in an air-fuel mixture into each cylinder. The system 100 may be configured to divert successive portions of the cooled gaseous fuel mixture from the cooler 130 into a micro-chamber 150, which may contain a plurality of micro-sensors, each configured to sense a characteristic of the gaseous fuel mixture. The characteristic of the gaseous fuel mixture may be output to a processor and used in a determination of a thermodynamic property of the gaseous fuel mixture. The thermodynamic property may be correlated by the processor, for example, with the levels of constituents in the composition of the gaseous fuel mixture 160, such as a mole percent of $O_2$, $H_2$, $N_2$, $NO_2$, CO, $CO_2$, and/or $CH_4$. In one exemplary embodiment the micro-chamber 150 may contain 4 spaced micro-sensors, with a resistance heater being associated with each of the micro-sensors. Each of the resistance heaters and micro-sensors may be a micro-electro-mechanical system (MEMS) made up of components that are between 1 to 1000 micrometers in size. The term "micro-sensor" as used herein may also include small devices, such as miniature transducers, that do not necessarily fall within the range from 1 to 1000 micrometers in size, but that are miniaturized devices and structures that may be manufactured using the techniques of microfabrication.

Each micro-sensor in the micro-chamber 150 may include a variable electrical resistor whose electrical resistance changes with respect to a change of its temperature. The variable electrical resistor for each micro-sensor may be a microheater situated in close proximity to the associated micro-sensor on a semiconductor substrate. The semiconductor substrate may be formed from a silicon or silicon-nitride chip, and may be positioned within the micro-chamber 150 to be at least partially surrounded by gas from each successive portion of the cooled gaseous fuel mixture introduced into the micro-chamber 150. The microheater may be supported above the substrate on suspending legs, or applied as a thin film resistor on a thin membrane connected to the substrate. Some examples of variable electrical resistors may include a nano-calorimeter, thermal conductivity sensor, micro-thermistor, a MEMS element, a micro-bolometer platform, a micro-wire, a micro-coil, or any variable electrical resistor device bonded or otherwise connected to the membrane, or supported proximal to the substrate by other means. Standard complementary metal-oxide-semiconductor (CMOS) fabrication processes, or MEMS fabrication processes, can be used to fabricate the electrical resistor device on the substrate. The substrate may consist of a silicon or silicon-nitride membrane including a CMOS electrical readout circuit or any CMOS integrated device. The substrate and micro-sensor devices may be partly or fully enclosed within a gas pressure environment comprising the successive portions of the cooled gaseous fuel mixture received into the micro-chamber 150 from the cooler 130. The environment including each micro-sensor may be filled with successive, relatively stationary volumes of the gaseous fuel mixture that exert pressure equally everywhere in the environment, including the top and bottom surfaces of the variable electrical resistors. The gaseous fuel mixture may include constituents such as $O_2$, $H_2$, $N_2$, $NO_2$, CO, $CO_2$, $CH_4$, and any other trace gases or pollutant gases.

Figure 2:
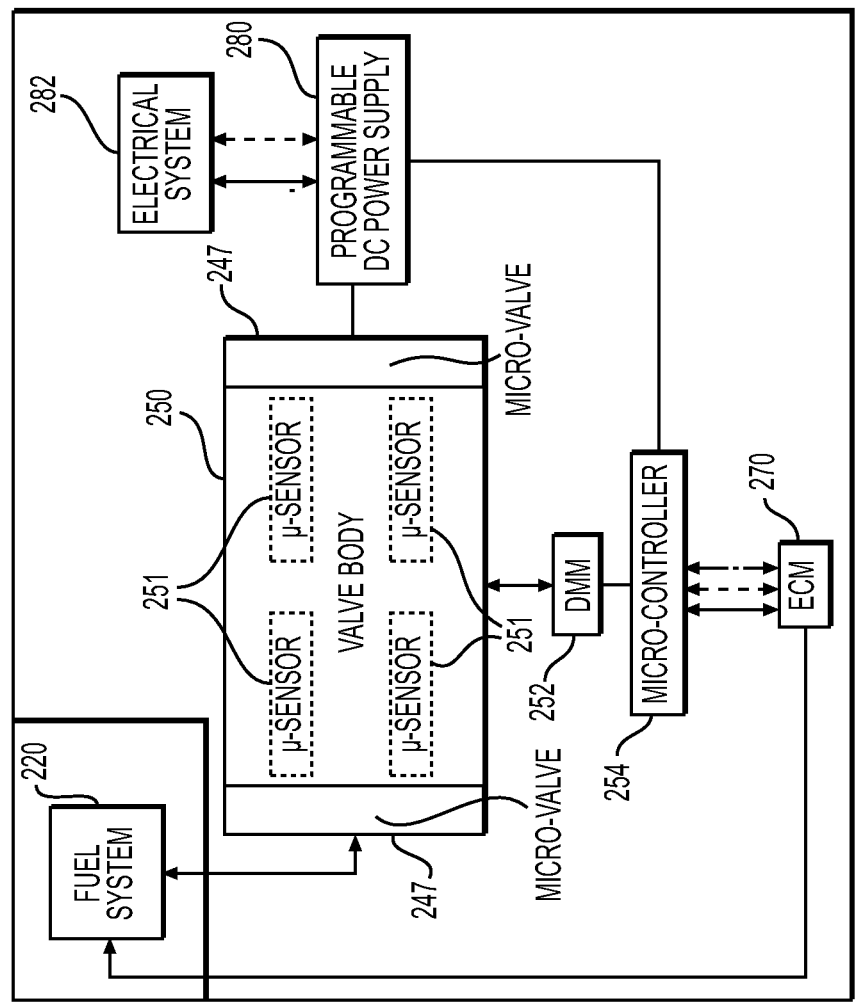
FIG. 2 is a diagrammatic illustration of an exemplary disclosed engine control system.

In the exemplary embodiment shown in FIG. 2, a micro-chamber 250 may contain 4 micro-sensors 251 spaced apart within the micro-chamber 250 and each provided with electrical power from an electrical power system 282. Piezo-electric micro-valves 247 may be provided at an inlet and an outlet of the micro-chamber 250 to control the flow of successive volumes of the gaseous fuel mixture supplied by the fuel system 220 into and out of the micro-chamber 250. The piezo-electric micro-valves 247 may also be actuated by DC power provided from a programmable DC power supply 280. The 4 micro-sensors 251 may be activated in parallel, and each of the variable resistors of each of the 4 micro-sensors 251 may receive a different voltage ($V_{heater}$) and current ($I_{heater}$) such that 4 different temperatures result at the 4 spaced locations in the micro-chamber 250 at substantially the same time. Reference to "substantially the same time" means that the 4 different micro-sensors all reach thermal equilibrium at different temperatures within 250 milliseconds (ms) after each successive volume of the gaseous fuel mixture has been introduced into the micro-chamber 250. The variable resistors of each of the micro-sensors 251 may receive sufficient voltage and current such that a temperature of each of the resistors is at least 10% greater than the temperature of the gaseous fuel mixture from the cooler 130 (FIG. 1), or from the fuel system 220 (FIG. 2). This minimum temperature difference between the gaseous fuel mixture introduced into the micro-chamber and the heated temperature of each of the resistors is sufficient to drive enough thermal transfer through the gas environment for an accurate indication of the thermal conductance of the system. Each of the microheaters associated with each micro-sensor may have a small enough heat radiation area such that it may be regarded as a thermal point source. The volume of gas surrounding each microheater may also be small enough so that a thermal equilibrium state may be achieved in less than 250 ms after introduction of each successive portion of the gaseous fuel mixture into the micro-chamber. A heat transfer coefficient of the gaseous mixture is therefore substantially in proportion to the thermal conductivity of the gaseous mixture.

One of ordinary skill in the art will recognize that alternative methods for introducing successive volumes of the gaseous fuel mixture into the micro-chamber 150 for testing, and then purging each of the successive volumes from the micro-chamber may be employed. One advantage of an arrangement such as shown in FIG. 2 is that actuation of the micro-valves 247 is very rapid, and may allow for a complete change of the volume of gas in the micro-chamber 250 approximately every 250 ms (approximately 4 times per second). The use of 4 different micro-sensors 251 arranged within the micro-chamber 250 and exposed to 4 different temperatures at substantially the same time also allows for the rapid determination of 4 data points on a thermodynamic property of each of successive volumes of the gaseous fuel mixture. Input and output voltages from the 4 different micro-sensors 251 may be used in the construction of a best fit linear regression model using partial least squares (PLS) methodology to estimate various parameters of the gaseous fuel mixture. Output signals from each of the micro-sensors 251 may be processed by a dynamic metrology module (DMM) 252, and a micro-controller 254 may use this information to send appropriate control signals to the programmable DC power supply 280. As successive volumes of the gaseous fuel mixture are analyzed by the DMM 252, the programmable DC power supply 280 may control the opening and closing of each of the micro-valves 247 to purge each successive volume and introduce another volume of the gaseous fuel mixture into the micro-chamber 250.

The temperature of each of the variable electrical resistors may be a function of applied electrical power and thermal transfers to the substrate and to the gaseous environment surrounding each variable electrical resistor within the micro-chamber 250. A voltage and/or current source may be connected to each of the variable electrical resistors of the micro-sensors 251 to electrically excite each resistor. Since each of the variable electrical resistor devices associated with each micro-sensor 251 is electrically resistive, this electrical excitation causes each resistor to heat to a particular temperature as a function of the applied electrical power by virtue of the Joule effect. The temperature of each variable electrical resistor at equilibrium is a function of the applied electrical power, thermal transfer to the substrate of the micro-sensor, and thermal transfer to the environment surrounding each micro-sensor via a plurality of heat transfer mechanisms such as conduction, convection, and radiation. The temperature at the substrate of each micro-sensor may be measured, for example, by a voltage output of a thermopile, one or more thermocouples, or other temperature detecting device mounted on the substrate. A system thermal conductance (G) of the gaseous fuel mixture and membrane of the associated micro-sensor may be calculated from $G=Q \Delta T$ where $Q=P$ (heating power). $P=V_{heater}I_{heater}$. The temperature difference of the thermopile or other temperature detecting device $\Delta T=V_{output}/S$, where S is the sensitivity of the thermopile or other temperature detecting device. $\Delta T$ is the temperature difference of the temperature detecting device. The temperature of the heater may be estimated from its resistance and from the heater's calibrated temperature-resistance response. Dynamically measured thermodynamic properties of the gaseous fuel mixture may be correlated directly to the composition of the gaseous fuel mixture.

In one embodiment, the method of sensing gas composition with a plurality of variable electrical resistor devices and micro-sensors may be based on probing the thermal response of each successive volume of gaseous fuel mixture introduced into the micro-chamber 250 with modulated electrical excitations. The thermal response may be determined by the thermal capacity and thermal conductivity of the gas in the environment surrounding each micro-sensor. In the thermal domain, the variable electrical resistor may have a low-pass characteristic, and the phase delay for each resistor may be accurately determined by the thermodynamic characteristics of the surrounding gas. The thermodynamic characteristics of the gas may be directly correlated to gas composition and pressure. Measurement of each resistor's phase delay in the thermal domain for each successive volume of gaseous fuel mixture introduced into the micro-chamber 250 will thus provide information about gas composition and pressure. The Joule heating comes from a periodically modulated electrical excitation, wherein the electrical excitation is modulated in time with a periodic electrical signal. The periodic electrical signal may be a sinusoidal signal, a square signal, a binary signal, a pulsed signal or any bounded periodic signal. The gas sensing method may include measuring the phase delay (or time delay) between the thermal response of the variable electrical resistor and the modulated electrical excitation. The phase delay (or the time delay) provides a real time measurement of the thermal capacity and thermal conductivity of the surrounding gas. Both thermal capacity and thermal conductivity may be correlated to gas composition and pressure, and continually updated as each successive volume of gaseous fuel mixture is introduced into the micro-chamber 250.

As shown in FIGS. 1 and 2, the ECM 170, 270 may be configured to use the determined percentages of one or more constituents in the gaseous fuel mixture to provide a control signal to a fuel mixing valve 180, as shown in FIG. 1, or the fuel system 220, as shown in FIG. 2. The fuel mixing valve 180 may operate in conjunction with a source for one or more of the constituents in order to make real-time adjustments to the levels of the one or more constituents during operation of the engine. As shown in FIG. 1, one example of a real-time adjustment to the level of a constituent in the gaseous fuel mixture may include a catalytic partial oxidation (CPOx) process 120 for producing reformed gas. The CPOx process 120 may be implemented during operation of the engine in conjunction with the fuel mixing valve 180 in order to provide additional amounts of $H_2$ in the gaseous fuel mixture. The addition of $H_2$ to the gaseous fuel mixture may improve thermal efficiency and combustion stability of the gaseous fuel mixture.

The CPOx process may be performed by a suitable catalyst in a fuel reformer associated with the system 100 and configured to reform a hydrocarbon fuel to a hydrogen-rich gas, mainly comprising CO, $H_2$, $CO_2$, and $H_2O$. The $H_2$-rich gas produced by the CPOx process may then be added to the gaseous fuel mixture using the fuel mixing valve 180 in amounts that are controlled by the ECM 170, and dependent upon the levels of $H_2$ detected in each successive volume of the gaseous fuel mixture by the micro-sensors in the micro-chamber 150.

Additional engine operational controls may be performed by the ECM 170, 270 based on the determined levels of various constituents in the gaseous fuel mixture. As is known in the art, a combustion engine may include a crankshaft that is rotatably disposed within an engine block. A connecting rod may connect each piston to a throw of the crankshaft so that a sliding motion of the piston between the TDC and BDC positions within each respective cylinder results in a rotation of crankshaft. Similarly, a rotation of the crankshaft may result in a sliding motion of each piston between the TDC and BDC positions. In a four-stroke engine, the piston may reciprocate between the TDC and BDC positions through an intake stroke, a compression stroke, a combustion or power stroke, and an exhaust stroke. In a two-stroke engine, a complete cycle may include a compression/exhaust stroke (BDC to TDC) and a power/exhaust/intake stroke (TDC to BDC). The cylinder head may define an intake passageway and an exhaust passageway. The intake passageway may direct compressed air or an air and fuel mixture from an intake manifold, through an intake opening and into each combustion chamber. The exhaust passageway may similarly direct exhaust gases from the combustion chamber through an exhaust opening and into an exhaust manifold. An intake valve may be disposed within an intake opening and configured to selectively engage a corresponding seat. Each intake valve may be movable between a first position, at which the intake valve engages the seat and inhibits a flow of fluid relative to the intake opening, and a second position, at which the intake valve is removed from the seat to allow the flow of fluid. An exhaust valve may be similarly disposed within an exhaust opening and configured to selectively engage a corresponding seat. Each exhaust valve may be movable between a first position, at which the exhaust valve engages the seat to inhibit a flow of fluid relative to the exhaust opening, and a second position, at which the exhaust valve is removed from the seat to allow the flow of fluid.

A series of valve actuation assemblies (not shown) may be operatively associated with the engine to move intake and exhaust valves between the first and second positions at desired timings relative to the rotation of the crankshaft and/or the position of each piston. Each cylinder head may include multiple intake openings and multiple exhaust openings. Each such opening may be associated with either an intake valve or an exhaust valve. The engine may include a valve actuation assembly for each cylinder head that is configured to actuate all of the intake valves or all of the exhaust valves of that cylinder head. A single valve actuation assembly could actuate the intake valves or the exhaust valves associated with multiple cylinder heads, if desired. The valve actuation assemblies may each embody, for example, a cam/push-rod/rocker arm arrangement, a solenoid actuator, a hydraulic actuator, and/or any other means for actuating known in the art. The timing at which intake and/or exhaust valves are opened and/or closed may have an effect on engine operation (e.g., an effect on cylinder pressure, temperature, efficiency, detonation timing, etc.), and may be variably controlled in some embodiments in accordance with the levels of one or more constituents detected in each successive volume of gaseous fuel mixture analyzed within the micro-chamber 150, 250.

The fuel system 220 shown in FIG. 2 may embody, for example, a fuel mixing valve, a fuel inlet valve, a fuel injector, a carburetor, etc. situated in communication with the intake passageway. The fuel system 220 may be powered electronically, hydraulically, mechanically, and/or pneumatically to pass pressurized fuel directly into each combustion chamber or indirectly via the intake passageway or a fuel rail system, as desired. The fuel may include a compressed gaseous fuel such as, for example, a mixture of natural gas, propane, bio-gas, landfill gas, hydrogen, and/or another fuel.

The amount of fuel allowed into the intake passageway and/or the timing at which the fuel is allowed into the intake passageway by the fuel system 220 may be associated with a ratio of air-to-fuel (A/F) introduced into each combustion chamber. Specifically, if it is desired to introduce a lean mixture of air and fuel (i.e., a mixture having a relatively low amount of fuel compared to the amount of air) into a combustion chamber, the fuel system 220 may cause fuel to be directed into the intake passage (and/or the combustion chamber) for a shorter period of time (or otherwise be controlled to inject less fuel per given cycle) than if a rich mixture of air and fuel (i.e., a mixture having a relatively large amount of fuel compared to the amount of air) is desired. Likewise, if a rich mixture of air and fuel is desired, the fuel system 220 may cause fuel to be directed into the intake passage (and/or the combustion chamber) for a longer period of time (or otherwise be controlled to inject more fuel per given cycle) than if a lean mixture is desired. The determination of various levels of constituents in the gaseous fuel mixture may be used by the ECM 270 as an input to assist in the regulation of operations of the engine (e.g., control of the intake valve, the exhaust valve, the fuel system 220, a load driven by the engine, etc.).

The DMM 252 and micro-controller 254 may be configured to receive the signals generated by each of the micro-sensors 251 within micro-chamber 250 approximately every 250 ms, and calculate one or more thermodynamic characteristics of the gaseous fuel mixture based on the signals. One of ordinary skill in the art will recognize that the frequency at which the DMM 252 and the micro-controller 254 may receive signals generated by the micro-sensors 251 may be varied depending on how rapidly each successive volume of gaseous fuel mixture may be supplied to and removed from the micro-chamber 250. The frequency at which signals may be received may also vary widely depending on how long it takes each volume of gaseous fuel to reach thermal equilibrium after activation of the micro-heaters associated with each micro-sensor. In the disclosed embodiment, the thermodynamic characteristic may be the system thermal conductance (G) of the gaseous fuel mixture. Other characteristics may include an Air-to-Fuel Ratio (A/F), a Lower Heating Value (LHV), a Wobbe index (WI), a Specific Gravity (Sg), a Methane Number (MN), and a Specific Heat Ratio (y). The micro-controller 254 may calculate the thermodynamic characteristics using one or more empirical formulas stored in memory.

The micro-controller 254 and the ECM 270 may each embody a single processor or multiple processors that include a means for controlling an operation of the engine system. Numerous commercially available processors may perform the functions of the micro-controller 254 and the ECM 270. The ECM 270 may also include or be associated with a memory for storing data such as, for example, an operating condition, design limits, performance characteristics or specifications of the engine system, operational instructions, and corresponding fuel quality parameters. Various other known circuits may be associated with the ECM 270, including power supply circuitry, signal-conditioning circuitry, solenoid driver circuitry, communication circuitry, and other appropriate circuitry. Moreover, the ECM 270 may be capable of communicating with other components of the engine system (e.g., with the valve actuation assemblies, the fuel system 220, the fuel mixing valve 180, the load driven by the engine, etc.) via either wired or wireless transmission and, as such, the ECM 270 may be connected to or alternatively disposed in a location remote from the engine.

The ECM 270 may be configured to adjust operation of the engine based on the fuel quality parameters and gaseous fuel mixture composition calculated by the micro-controller 254. For example, the ECM 270 may be capable of causing intake and/or exhaust valves to open earlier relative to the movement of the piston, to stay open longer, and/or to open by a different lift amount. This change in valve timing may have an effect on an amount of air and/or fuel allowed into the combustion chamber, and a resulting pressure, temperature, efficiency, and/or emissions. Likewise, the ECM 270 may be capable of causing the fuel system 220 to deliver more or less fuel at any desired timing into the intake passage (and/or into the combustion chamber) to thereby change an air-to-fuel ratio of the engine and affect a resulting speed output, power output, efficiency, emissions, etc. The ECM 270 could also be capable of changing a load on the engine, for example by increasing or decreasing the load. The ECM 270 could affect engine operation in other ways as well.

Figure 3:
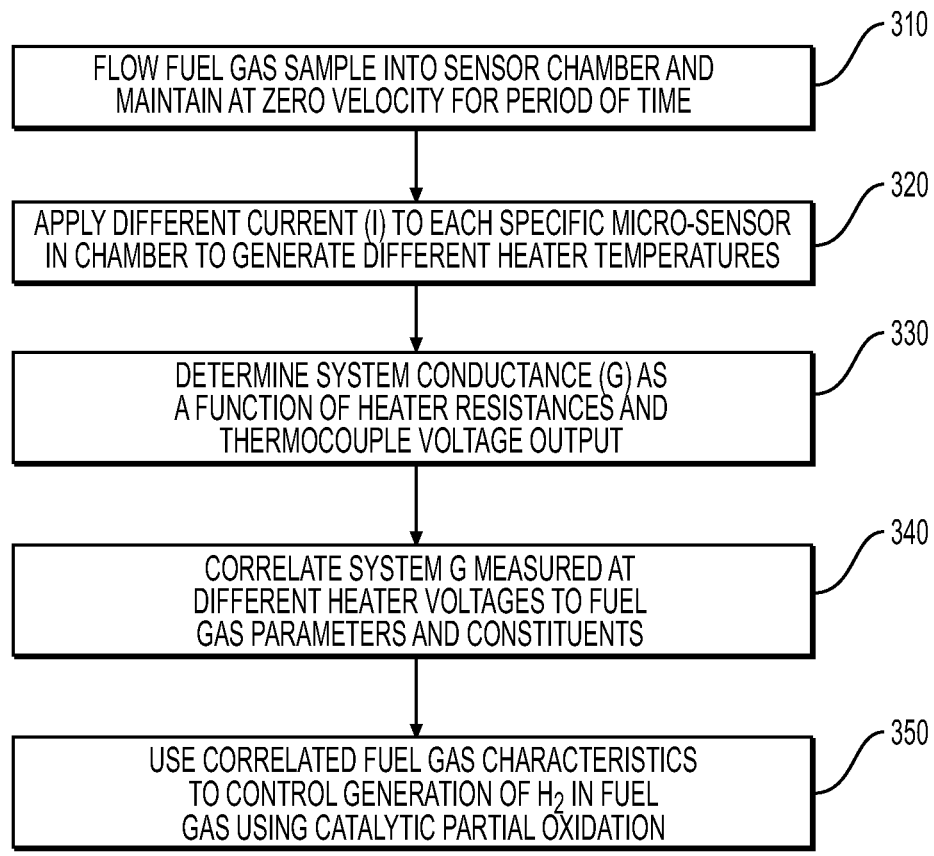
FIG. 3 is a flowchart depicting an exemplary disclosed method that may be performed by the system of FIG. 1.

The ECM 270 may also adjust engine operation based on the thermodynamic characteristics and composition of the gaseous fuel mixture to improve operation under a given set of conditions. That is, based on the gaseous fuel mixture characteristics, the ECM 270 may change engine operation so as to avoid damaging situations (e.g., engine knock, over pressure, over temperature, etc.), improve efficiency and/or power output, and/or to accomplish other user-specified goals. FIG. 3 shows a flowchart depicting a method of sensing and controlling fuel gas constituent levels based on a thermodynamic characteristic of the fuel. FIG. 3 will be discussed in more detail in the following section to further illustrate the disclosed concepts.

INDUSTRIAL APPLICABILITY

The disclosed system may have industrial applicability in situations involving a changing fuel supply, or gaseous fuel mixture of unknown composition, where continued operation of the associated engine at high levels of performance and reduced levels of pollutants is desired. The disclosed system may help ensure continued operation by selectively implementing engine-protecting adjustments based on changing fuel quality parameters that are detected by the system. The disclosed engine system may also help ensure high-level engine performance by selectively implementing adjustments to the amounts of one or more constituents in the gaseous fuel mixture supplied to the engine in order to achieve desired engine operating parameters. One exemplary process for sensing and controlling the amount of a constituent in the gaseous fuel mixture is shown in FIG. 3.

As shown in FIG. 3, the first step (Step 310) may include flowing a fuel gas sample into a sensor chamber (micro-chamber 250) and maintaining the fuel gas sample in the micro-chamber 250 at substantially zero velocity for a period of time. As discussed above, the small volume of the micro-chamber 250 may allow thermal equilibrium to be reached rapidly, such as in 250 ms or less, thereby enabling the system to effectuate a rapid succession of gas samples for determination of a particular thermodynamic characteristic and composition of the gas.

The second step (Step 320) may include applying a different current ($I_{heater}$) and/or voltage ($V_{heater}$) to a micro-heater associated with each specific micro-sensor 251 in the micro-chamber 250 in order to generate a different heater temperature at each of the micro-sensors 251. After each microheater and the surrounding gas reaches thermal equilibrium, the third step (Step 330) may include determining a system conductance (G) as a function of the heater resistances ($R_{heater}$), and a thermopile voltage output ($V_{output}$) at the substrate of each micro-sensor. As discussed above, the system thermal conductance $G=(SV_{heater} I_{heater})/V_{output}$. S is the sensitivity of the thermopile or other temperature detecting device. Temperature may be measured by a thermopile, one or more thermocouples, or other temperature detecting device.

After determination of the system thermal conductance G, the fourth step (Step 340) may include correlating the system conductance G, the heater temperature T, and the thermopile output voltage $V_{output}$ measured at the different heater voltages ($V_{heater}$) and currents ($I_{heater}$) to fuel gas parameters and constituents. The dynamic metrology module (DMM) 252, micro-controller 254, and engine control module 270 may then use the correlated fuel gas characteristics at the fifth step (Step 350) to control generation of $H_2$ to be supplied to the fuel gas mixture by using a catalytic partial oxidation (CPOx) reforming process. The addition of $H_2$ to the gaseous fuel mixture may improve thermal efficiency and combustion stability of the gaseous fuel mixture, thereby maintaining or improving the performance of the engine while reducing emissions.

The disclosed system may provide several benefits. First, the disclosed system may be relatively simple, having only one type of micro-sensor, e.g., a micro-sensor capable of sensing the thermal conductivity of a gas. This simplicity may help to reduce a cost of the system 100. In addition, by simultaneously determining thermodynamic properties of the gaseous fuel mixture at multiple locations within a micro-chamber 150, 250, an accuracy of the measurement may be increased. In particular, a theoretical accuracy has been calculated for a system employing 4 micro-sensors 251 within a micro-chamber 250, wherein electrical power is provided to each of the 4 microheaters of the 4 micro-sensors 251 to result in temperatures at each of the micro-sensors of 98, 158, 218, and 278° C. The simulated capability for this system using ideal gas law has been determined to enable calculation of the mole percent of $H_2$, CO, $CO_2$, $CH_4$, and $N_2$ to an accuracy of less than ±1% full scale (wherein the full scale accuracy (FS) is the best fit to a straight line using a partial least squares PLS linear regression methodology). Further, because only a single thermodynamic property is required to determine a corresponding gaseous fuel mixture composition, the system may be responsive, allowing for wide application in transient systems.

It will be apparent to those skilled in the art that various modifications and variations can be made to the system of the present disclosure. Other embodiments of the system will be apparent to those skilled in the art from consideration of the specification and practice disclosed herein. It is intended that the specification and examples be considered as exemplary only, with a true scope of the disclosure being indicated by the following claims and their equivalents.

What is claimed is:

1. A system for sensing and controlling a fuel gas composition, the system comprising:
   a plurality of micro-sensors mounted in a single chamber configured to hold each of a successive portion of a mixture of gaseous fuel at substantially zero velocity for a period of time, each of said micro-sensors being configured to sense a characteristic of a mixture of gaseous fuel introduced into the chamber;
   a plurality of heating elements, each of said heating elements being associated with one of said plurality of micro-sensors, and said plurality of heating elements being configured to implement a different temperature level at each of the micro-sensors; and
   a microprocessor configured to:
      determine a thermodynamic property of the mixture of gaseous fuel at the different temperature levels at each of the micro-sensors as a function of the characteristic sensed by each micro-sensor;
      correlate the thermodynamic property to a fuel gas composition of the mixture of gaseous fuel; and
      control an amount of at least one constituent in the mixture of gaseous fuel as a function of the fuel gas composition determined by the correlation.

2. The system of claim 1, wherein the thermodynamic property is a thermal conductivity of the mixture of gaseous fuel.

3. The system of claim 1, wherein the microprocessor is configured to determine the thermodynamic property as a function of at least one of a voltage and a current applied to each of the heating elements associated with each of the micro-sensors.

4. The system of claim 1, wherein the microprocessor is configured to determine the thermodynamic property as a function of electrical power supplied to each of the plurality of heating elements, and a temperature sensed at each of the associated micro-sensors.

5. The system of claim 4, wherein the microprocessor is configured to receive a voltage signal indicative of a temperature sensed by a thermopile positioned on a substrate of each of the micro-sensors after the mixture of gaseous fuel at each of the micro-sensors has reached thermal equilibrium following supply of the electrical power to each of the plurality of heating elements.

6. The system of claim 1, wherein the microprocessor is configured to control the amount of $H_2$ in the mixture of gaseous fuel.

7. The system of claim 6, wherein the microprocessor is configured to:
   control a generation of the amount of $H_2$ by controlling a catalytic partial oxidation process performed by a reformer to generate $H_2$; and
   control addition of the $H_2$ produced by the reformer to the mixture of gaseous fuel.

8. The system of claim 1, wherein the microprocessor is further configured to control an operating parameter of an engine configured to combust the mixture of gaseous fuel based at least in part on the amount of the at least one constituent in the mixture of gaseous fuel.

9. The system of claim 8, wherein the engine operating parameter is at least one of an air/fuel ratio, an ignition timing, a fuel injection timing, a fuel injection amount, or a load on the engine.

10. A control system for use with an engine, the control system comprising:
    a plurality of micro-sensors mounted in a single micro-chamber configured to hold each of a successive portion of a mixture of gaseous fuel at substantially zero velocity for a period of time, each of the plurality of micro-sensors being configured to sense a characteristic of a mixture of gaseous fuel introduced into the micro-chamber;
    a plurality of resistive heating elements associated with each of the plurality of micro-sensors, each of the plurality of resistive heating elements being configured to implement a different temperature level at each of the plurality of micro-sensors; and
    a microprocessor configured to:
       determine a thermodynamic property of the mixture of gaseous fuel at the different temperature levels at each of the micro-sensors as a function of the characteristic sensed by each micro-sensor;
       correlate the thermodynamic property to a fuel gas composition of the mixture of gaseous fuel; and
       control an amount of at least one constituent in the mixture of gaseous fuel and an operating parameter of the engine as a function of the fuel gas composition determined by the correlation.

11. The control system of claim 10, wherein the thermodynamic property is a thermal conductivity of the mixture of gaseous fuel.

12. The control system of claim 10, wherein the microprocessor is configured to determine the thermodynamic property as a function of at least one of a voltage and a current applied to each of the heating elements associated with each of the micro-sensors.

13. The control system of claim 10, wherein the microprocessor is configured to determine the thermodynamic property as a function of electrical power supplied to each of the plurality of heating elements, and a temperature sensed at each of the associated micro-sensors.

14. The control system of claim 13, wherein the microprocessor is configured receive a voltage signal indicative of a temperature sensed by a thermopile positioned on a substrate of each of the micro-sensors after the mixture of gaseous fuel at each of the micro-sensors has reached thermal equilibrium following supply of the electrical power to each of the plurality of heating elements.

15. The control system of claim 10, wherein the microprocessor is configured to control the amount of $H_2$ in the mixture of gaseous fuel.

16. The control system of claim 15, wherein the microprocessor is configured to:
    control a generation of the amount of $H_2$ by controlling a catalytic partial oxidation process performed by a reformer to generate $H_2$; and
    control addition of the $H_2$ produced by the reformer to the mixture of gaseous fuel.

17. The control system of claim 16, wherein the microprocessor is further configured to control an engine operating parameter based at least in part on the amount of the at least one constituent in the mixture of gaseous fuel.

18. The control system of claim 17, wherein the engine operating parameter is one of an air/fuel ratio, an ignition timing, a fuel injection timing, a fuel injection amount, or a load on the engine.

19. A method of controlling an engine, comprising:
    diverting successive portions of a mixture of gaseous fuel being supplied to the engine into a micro-chamber;
    temporarily holding each of the successive portions in a substantially still condition within the micro-chamber;

heating each of a plurality of micro-sensors to a different temperature level at the same time at a plurality of different spaced locations within the micro-chamber;

determining an overall thermal conductance for each successive portion of the mixture of gaseous fuel; and selectively adjusting at least one of a level of a constituent present in the mixture of gaseous fuel and a control parameter of the engine based on the thermal conductance.

20. The method of claim 19, further including:

receiving a voltage output signal indicative of a temperature sensed by a thermopile positioned on a substrate of a micro-sensor located at each of the spaced locations within the micro-chamber after each successive portion of the mixture of gaseous fuel at each micro-sensor has reached thermal equilibrium following supply of electrical power to a microheater associated with the micro-sensor; and determining the overall thermal conductance for each successive portion as a function of the electrical power divided by the voltage output.

* * * * *